United States Patent [19]

Manabe et al.

[11] Patent Number: 5,236,495
[45] Date of Patent: Aug. 17, 1993

[54] CALCIUM PHOSPHATE TYPE GLASS-CERAMIC

[75] Inventors: Tsuneo Manabe; Hirosi Usui, both of Yokohama; Yasuko Osaki, Kawasaki, all of Japan

[73] Assignee: Asahi Glass Company Ltd., Tokyo, Japan

[21] Appl. No.: 747,978

[22] Filed: Aug. 21, 1991

[30] Foreign Application Priority Data

Aug. 21, 1990 [JP] Japan .................................. 2-218171
Nov. 20, 1990 [JP] Japan .................................. 2-312805
Dec. 27, 1990 [JP] Japan .................................. 2-414998

[51] Int. Cl.$^5$ ............................................. C03C 10/02
[52] U.S. Cl. .............................................. 106/35; 501/1; 501/10; 501/45; 501/48
[58] Field of Search ............... 106/35; 501/1, 10, 45, 501/48

[56] References Cited

U.S. PATENT DOCUMENTS

| | | | |
|---|---|---|---|
| 4,198,244 | 4/1980 | Binns et al. .................. | 106/35 |
| 4,617,279 | 10/1986 | Manabe et al. ................ | 501/10 |
| 4,626,514 | 12/1986 | Watanabe et al. ............. | 501/45 X |
| 4,681,633 | 7/1987 | Watanabe et al. ............. | 501/10 X |
| 4,698,318 | 10/1987 | Vogel et al. .................. | 501/10 |
| 4,781,744 | 11/1988 | Kobayashi et al. ............ | 501/10 X |
| 4,943,541 | 7/1990 | Watanabe et al. ............. | 501/10 |
| 5,024,973 | 6/1991 | Kondo et al. .................. | 501/10 |

FOREIGN PATENT DOCUMENTS 60-210546 10/1985 Japan .
62-52142 3/1987 Japan .
63-260839 10/1988 Japan .

*Primary Examiner*—Karl Group
*Attorney, Agent, or Firm*—Oblon, Spivak, McClelland, Maier & Neustadt

[57] ABSTRACT

A calcium phosphate type glass-ceramic which comprises from 64 to 72% by weight of phosphorus oxide in terms of $P_2O_5$, from 13 to 20% by weight of calcium oxide in terms of CaO, from 6 to 13% by weight of strontium oxide in terms of SrO, and from 3 to 15% by weight in total of at least one member selected from the group consisting of aluminum oxide, cerium oxide and lanthanum oxide respectively in terms of $Al_2O_3$, $Ce_2O_3$ and $La_2O_3$, a molar ratio of $(CaO+SrO)/P_2O_5$ being 0.78–0.86.

5 Claims, No Drawings

CALCIUM PHOSPHATE TYPE GLASS-CERAMIC

The present invention relates to a calcium phosphate type glass-ceramic, particularly to a calcium phosphate type glass-ceramic suitable for using as a dental material.

Heretofore, a calcium phosphate type glass-ceramic is known to be useful as a dental material since it has an excellent castability, a high mechanical strength and an outer appearance similar to that of a natural tooth. Japanese Unexamined Patent Publication Nos. 260839/1988 and 210546/1985 disclose a calcium phosphate type glass-ceramic containing strontium oxide as a dental material.

However, there was no dental material that has sufficient mechanical strength and chemical resistance durable for use in a mouth for a long time and that has a high translucency similar to that of a natural tooth in view of an external appearance.

In the case of a calcium phosphate type glass, there was a tendency that a chemical resistance became lowered when a composition was prepared for aiming to obtain a glass-ceramic having a high external translucency and a high mechanical strength. On the contrary, there was a tendency that a translucency and a strength became lowered when a composition was prepared for aiming to obtain a crystallized glass having a high chemical resistance. Therefore, it was very difficult to obtain a satisfactory chemical resistance when an aesthetically highly appreciated translucency is required.

We have studied for aiming to obtain a glass-ceramic having not only a satisfactory aesthetically highly appreciated translucency but also a high mechanical strength and a high chemical resistance, suitable for use as a dental material, and have discovered as a result of the study that the above aim can be achieved by crystallizing a calcium phosphate type glass composition, the calcium component of which is substituted with a specific amount of strontium.

Thus, the present invention is to provide a calcium phosphate type glass-ceramic which comprises from 64 to 72% by weight of phosphorus oxide in terms of $P_2O_5$, from 13 to 20% by weight of calcium oxide in terms of CaO, from 6 to 13% by weight of strontium oxide in terms of SrO, and from 3 to 15% by weight in total of at least one member selected from the group consisting of aluminum oxide, cerium oxide and lanthanum oxide respectively in terms of $Al_2O_3$, $Ce_2O_3$ and $La_2O_3$, a molar ratio of $(CaO+SrO)/P_2O_5$ being 0.78–0.86.

In the present invention, an amount of phosphorus oxide should be from 64 to 72% by weight in terms of $P_2O_5$. If the amount of $P_2O_5$ is less than 64% by weight, microcracks occur between crystal particles at the time of crystallization, thereby producing a glass-ceramic having a low mechanical strength and a low translucency. On the contrary, if the amount of $P_2O_5$ exceeds 72% by weight, a glass-ceramic having a low chemical resistance is obtained.

An amount of calcium oxide should be from 13 to 20% by weight in terms of CaO. If the amount of CaO is less than 13% by weight, a glass-ceramic having a low chemical resistance is obtained. On the contrary, if the amount of CaO exceeds 20% by weight, microcracks occur between crystal particles at the time of crystallization, thereby producing a glass-ceramic having a low mechanical strength and a low translucency.

An amount of strontium oxide should be from 6 to 13% by weight in terms of SrO. If the amount of SrO is less than 6% by weight, the mechanical strength of the product is unsatisfactorily low. On the contrary, the amount of SrO exceeds 13% by weight, the chemical resistance of the product is unsatisfactorily low.

The total amount of aluminum oxide, cerium oxide and lanthanum oxide should be from 3 to 15% by weight respectively in terms of $Al_2O_3$, $Ce_2O_3$ and $La_2O_3$. If the total amount of $Al_2O_3$, $Ce_2O_3$ and $La_2O_3$ is less than 3% by weight, the chemical resistance of the product is unsuitably low. On the contrary, if the total amount of $Al_2O_3$, $Ce_2O_3$ and $La_2O_3$ exceeds 15% by weight, a glass-ceramic having an unsuitably low translucency is obtained. Also, it is preferable that each amount of $Al_2O_3$, $Ce_2O_3$ and $La_2O_3$ should not exceed 5% by weight. If each amount of $Al_2O_3$, $Ce_2O_3$ and $La_2O_3$ exceeds 5% by weight, a glass-ceramic having an unpreferably low translucency tends to be produced.

A molar ratio of $(CaO+SrO)/P_2O_5$ should be 0.78–0.86. If the molar ratio of $(CaO+SrO)/P_2O_5$ is less than 0.78, the chemical resistance of the product is unsuitably low. On the contrary, if the molar ratio of $(CaO+SrO)/P_2O_5$ exceeds 0.86, a glass-ceramic having an unsuitably low mechanical strength and low translucency is obtained.

Among the above compositions of these ranges, the most improved translucency, mechanical strength and chemical resistance can be provided by using a composition comprising from 65 to 69% by weight of $P_2O_5$, from 15 to 20% by weight of CaO, from 7 to 11% by weight of SrO and from 5 to 10% by weight in total of $Al_2O_3$, $Ce_2O_3$ and $La_2O_3$, a molar ratio of $(CaO+SrO)/P_2O_5$ being 0.80–0.84.

In the preparation of a glass-ceramic of the present invention, the following materials are used as starting materials.

As a phosphorus material, there are enumerated phosphoric acids such as orthophosphoric acid or ammonium salts of these phosphoric acids. Further, calcium salts of phosphoric acids such as calcium phosphate and calcium hydrogen phosphate may be used in a mixture with other calcium compounds and phosphorus compounds. Furthermore, aluminum slats of phosphoric acids such as aluminum phosphate may be used in a mixture with other aluminum compounds and phosphorus compounds.

As a calcium or strontium material, there are typically enumerated their oxides or carbonates, but other hydroxides, organic salts such as oxalates and acetates, and inorganic salts may optionally be used.

As aluminum, cerium and lanthanum materials, oxides are preferably used, but other hydroxides and sulfates which can be converted into oxides by heating can also be used.

The glass-ceramic composition of the present invention may further contain fluorine in an amount of from 0.01 to 5% by weight in terms of an F atom which improves toughness and workability.

The amount of fluorine should be from 0.01 to 5% by weight in terms of F atom. If the amount of fluorine is less than 0.01% by weight, the effect of the addition is not satisfactorily achieved. An appropriate amount of fluorine remarkably improves the toughness of a glass-ceramic, but if the amount of fluorine exceeds 5% by weight, the mechanical strength and the translucency of the glass-ceramic become unsuitably poor. When fluorine is added to a calcium phosphate type glass-ceramic, the fluorine atom is present in the form of substituting an oxygen atom.

As a fluorine material, it is preferable to use a compound wherein a part of the above-mentioned metal ion materials is converted into a fluoride. Any type of metal fluorides can finally produce substantially the same glass-ceramic after a glass melting step. For example, calcium fluoride, aluminum fluoride, fluorine-containing apatite are usable.

In a usual melting step, there is a possibility that the fluorine component added in this manner is partly volatilized. An amount of fluorine to be volatilized depends on the melting condition, but the effect of the addition of fluorine can be achieved so long as the fluorine is present in the glass-ceramic in an amount of the above-mentioned range.

The glass-ceramic of the present invention may further contain at least one element selected from Dy, Pr, Tb and Eu in an amount of from 0.001 to 5 mol %, which provide fluorescent properties similar to that of a natural tooth. Thus, a dental material having an external appearance quite similar to that of a natural tooth even in the dark, can be obtained.

That is, Dy, Pr, Tb and Eu are elements which provide fluorescence in the same manner as a natural tooth when they are added to a calcium phosphate type glass to be crystallized. Among them, Dy is most preferable since it provides fluorescence closest to that of a natural tooth in respect of color tone and strength of fluorescence.

Dy, Pr, Tb and Eu should be added alone or in a mixture of two or more in an amount of from 0.001 to 5 mol %. If the amount is less than 0.001 mol %, a satisfactory fluorescent color can not be exhibited, and the external appearance of the product becomes poor in the dark as compared with a natural tooth. On the contrary, if the amount exceeds 5 mol %, a satisfactory fluorescent color is not exhibited due to quenching in fluorescence and the color of the product becomes unbalanced as compared with a natural tooth. Among the above-mentioned ranges, a preferable range is from 0.05 to 1 mol %, and if these additives are added in an amount of within the above preferable range, the external appearance of the product becomes quite similar to that of a natural tooth.

The term "mol %" means a value calculated on the basis of the total mol number of respective single metal oxides of the oxide components which constitute a calcium phosphate glass-ceramic. For example, a phosphoric acid component is calculated in terms of $P_2O_5$, and a calcium oxide component is calculated in terms of CaO. Each mol number of Dy, Pr, Tb and Eu metal elements is expressed in % to the total mol number of the respective components.

Dy, Pr, Tb and Eu may be added to glass melt starting material respectively alone or in a mixture of two or more metals in an appropriate form of an oxide, a hydroxide, a halide, a sulfide, a nitrate, a sulfate or an organic acid salt.

The glass-ceramic of the present invention is prepared as a homogeneous glass from the above-mentioned starting materials. For example, such a glass can be prepared by weighing a predetermined amount of each of the above-mentioned starting materials to prepare a mixture, calcining the resultant mixture at a temperature of from 200° to 900° C. for from 1 to 10 hours, and then melting the calcined product in a platinum crucible at a temperature of from 900° to 1,500° C. for from 5 minutes to 10 hours.

The glass thus obtained is optionally shaped at the time of solidifying by cooling or after solidifying, and is then crystallized by heat treatment to obtain a crystallized glass. The crystallizing treatment may be conducted by heating a glass cooled once to around room temperature to a crystallizing temperature again or by cooling a glass melt to a crystallizing temperature below the softening point of the glass.

The glass-ceramic of the present invention can be suitably used as a dental material for repairing a crown of a tooth. The melt of the glass-ceramic composition of the present invention can be precisely cast in the same manner as conventional metallic dental materials for a crown of a tooth.

A crown of the glass-ceramic of the present invention can be prepared in accordance with the following process. The above melted glass-ceramic composition (a glass-ceramic composition once solidified may be melted again) is cast and molded in a mold prepared by lost wax process in the same manner as conventional metallic dental materials. A centrifugal casting machine, a vacuum pressure casting machine and a pressure casting machine can be suitably used as a casting device.

The product thus cast is then crystallized in a mold or after taking out from the mold by maintaining at a temperature of from 500° to 900° C. for from 5 minutes to 100 hours. It is more preferable to crystallize a cast product in a mold since the change in size or deformation is reduced. When the cast product is crystallized after taking out from the mold, there are advantages that casting defects can be checked at the time of transparent glass state and that crystallization can be conducted after correcting a shape. In this case, the shape can be prevented from being deformed by investing the glass product in alumina powder or in such a material as the above-mentioned investment material unreactive with the glass product at the crystallization temperature when it is crystallized.

In the present invention, it is preferable that there is a calcium phosphate crystal present on the surface of a mold to be in contact with a calcium phosphate type glass to be crystallized.

It is considered that the calcium phosphate crystal present in the mold works as a seed crystal for growing a crystal from a glass composition. Therefore, the crystallization in the vicinity of the surface of a crystallized glass is uniformly effected, thereby producing a glass-ceramic having a dense structure. Consequently, the toughness and the mechanical strength of the glass-ceramic are improved. Particularly, when a calcium phosphate crystal solid-solubilized with strontium is used, the crystallization is more uniformly effected and the structure of the glass-ceramic thus obtained is more preferably densified.

In the calcium phosphate crystal solid-solubilized with strontium, the solid solution amount of strontium solid-solubilized in the calcium phosphate crystal is preferably close to a solid solution amount of strontium in a calcium phosphate crystal grown from the glass. According as the solid solution amounts of strontium in the two materials are closer to each other, it works more effectively as a seed crystal and consequently a crystal grows more uniformly by heat treatment, thereby producing a glass-ceramic having a high toughness. For example, there can be effectively used a calcium phosphate crystal solid-solubilized with strontium wherein 1 to 90 mol % of calcium is substituted with strontium depending on the glass composition.

The calcium phosphate seed crystal is not necessarily a single phase, but may contain a crystal which does not work as a seed crystal. Its composition is preferably close to that of a crystal grown from the glass composition. Thus, the composition of the seed crystal preferably comprises from 0.5 to 50 mol % of strontium oxide in terms of SrO, from 0.5 to 50 mol % of calcium oxide in terms of CaO and from 30 to 70 mol % of phosphorus oxide in terms of $P_2O_5$. Among them, a more preferable composition comprises from 1 to 20 mol % of strontium oxide in terms of SrO, from 30 to 50 mol % of calcium oxide in terms of CaO and from 40 to 60 mol % of phosphorus oxide in terms of $P_2O_5$.

In the present invention, the calcium phosphate seed crystal may have only to be present in the vicinity of the surface of a mold, and if necessary, it may be incorporated in the whole body of the mold. The amount of calcium phosphate crystal to be present in the mold is determined depending on the material of the mold, but it is generally preferable that the calcium phosphate crystal should be present at least 3% by weight, more preferably at least 20% by weight to a depth of at least 10 $\mu$m, more preferably at least 100 $\mu$m from the surface of the mold.

A method for producing the calcium phosphate crystal is not specially limited, but there are various methods. For example, after preparing an $SrO-CaO-P_2O_5$ system glass having a desired composition, the glass composition thus prepared is crystallized by heat treatment and is then pulverized.

These calcium phosphate crystals may have only to be a crystal when a molding material is actually used as a mold, and therefore it is not always necessary to use a calcium phosphate crystal from the first stage as a starting material for a mold. For example, a calcium phosphate type glass, calcium phosphate compounds such as $CaH_4(PO_4)_2$ and/or a strontium-containing compound are mixed with a mold material, and a calcium phosphate crystal may be grown in the mold material by heat of a casting process. The mold having the calcium phosphate crystal thus grown can be satisfactorily used.

In the present invention, a base material for a mold having a calcium phosphate crystal incorporated, is not specially limited, but there can be optionally used, for example, magnesium phosphate type, silicate type, alumina type, aluminum phosphate type, zirconia type, or gypsum type compounds.

The calcium phosphate crystal to be present in the mold, preferably has a small particle diameter. According as the particle diameter is larger, the amount of crystal to be incorporated for achieving the desired effect tends to increase. If the particle diameter of the crystal exceeds 100 $\mu$m, the desired effect can not be satisfactorily achieved even when the amount of the crystal is increased. The increase in the amount of the crystal added is not preferable since it reduces the smoothness of the surface of the mold.

The mold used in the present invention can be prepared, for example, in the following manner. For example, a calcium phosphate crystal having an average particle diameter of not larger than 100 $\mu$m is previously incorporated in a base material for a mold, and the resultant mixture is cured in accordance with a usual method, thereby producing a mold having the calcium phosphate crystal dispersed in the whole body of the mold. Also, a mold having a calcium phosphate crystal present on the surface only may be prepared by coating the calcium phosphate crystal together with a suitable binder and an aggregate on the surface of a mold previously prepared. Further, a mold may be prepared by forming a layer of a mixture of a calcium phosphate crystal with a suitable binder and an aggregate on the surface of a master mold (e.g. a wax pattern in the case of lost wax process) by coating or dipping, curing a base mold material in the master mold having the above prepared layer and then removing the master mold by calcining.

A preferable method for producing a glass-ceramic by using the above mold of the present invention, comprises melting a calcium phosphate type glass, casting the melt in the mold heated to a suitable temperature and crystallizing the cast glass as it is without taking it from the mold. A method for crystallization is not specially limited, but crystallization may be conducted by maintaining the cast glass for a predetermined time in an electric furnace maintained at the crystallization temperature of the glass. After the crystallization, the glass-ceramic is cooled to around room temperature and is taken out from the mold.

In the case of casting a melt of calcium phosphate type glass in a mold having a calcium phosphate crystal incorporated, if the amount of the calcium phosphate crystal incorporated in the mold is too large, a reaction tends to occur between the mold material and the calcium phosphate type glass and therefore it becomes difficult to release and to remove the cast-molded product from the mold. In such a case, it is effective for improving release properties to incorporate powdery boron nitride, carbon or the like together with powdery calcium phosphate crystal in the mold. Among them, boron nitride is particularly preferable as a release agent.

In the above glass composition, a calcium phosphate crystal grown from the glass composition is preferably calcium $\beta$-metaphosphate crystal solid-solubilized with strontium, and therefore a calcium phosphate used as a mold material is also preferably a calcium metaphosphate crystal, particularly calcium $\beta$-metaphosphate crystal.

Furthermore, the present invention can be applied also for crystallizing a calcium phosphate type glass which is cast in an ordinary mold and is taken out as it is, or for crystallizing a glass molded product obtained by press molding or other methods. Particularly, when a glass molded product is subjected to crystallization after being coated with a base material having a calcium phosphate crystal incorporated and wrapped with alumina powder, the calcium phosphate crystal in contact with the surface of the glass molded product works as a seed crystal, thus producing more uniformly crystallized glass-ceramic. According to such a process, there is an advantage that crystallization can be conducted after checking cast defects and correcting the shape of the molded product, when it is taken out.

When crystallization is conducted in an investment material, a crystallized glass is taken out from the investment material after the crystallization to cut a sprue part (runner) and a crystallized glass crown of a tooth can be obtained by being subjected to surface finish process including polishing.

In the present invention, the color tone of a crystallized glass can be adjusted quite similar to that of a natural tooth by incorporating one or more metal elements selected from Ni, Fe, Co, Rh, Ru and Pd metal alone or their compounds in an amount of from 0.001 to 3.0% by weight in total. As the starting materials, there can be used metal alone, oxides and compounds convertible into oxides when fusing glass, for example, hydroxides, sulfides, halides, carbonates, organic acid salts and the like.

Furthermore, in the present invention, at least one of oxides of Li, Na and K can be added in an amount of from 0.01 to 15% by weight respectively in terms of $Li_2O$, $Na_2O$ and $K_2O$. These additives improve the mechanical strength of a glass-ceramic. If the amount of these additives is less than 0.01% by weight, the effect of the additives can not be satisfactorily achieved. On the contrary, if the amount of these additives exceeds 15% by weight, the chemical durability of a glass-ceramic is lowered. As the starting materials of Li, Na and K, there can be used, in addition to oxides, single substances, hydroxides, carbonates, nitrates, sulfates, halides, organic acid salts and the like.

The present invention will be described in detail with reference to typical Examples. However, it should be understood that the present invention is by no means restricted to such specific Examples.

EXAMPLES 1 TO 7

The starting materials were mixed in an amount of 400 g in total at such mixing ratios as to provide the composition shown in Table 1 at the time of glass formation, and the resultant mixture was fully mixed. After calcining the mixture at 400° C. for 5 hours, the mixture was melted in a platinum crucible at 1,300° C. for 2 hours. Thereafter, the melt was cast on a stainless steel plate, thereby quenching to obtain a glass.

TABLE 1

| Examples | Composition (% by weight) | | | | | | | $\frac{(CaO + SrO)}{P_2O_5}$ |
|---|---|---|---|---|---|---|---|---|
| | $P_2O_5$ | CaO | SrO | $Al_2O_3$ | $Ce_2O_3$ | $La_2O_3$ | Others | |
| 1 | 67.9 | 18.6 | 6.7 | 3.8 | 3.0 | 0 | | 0.83 |
| 2 | 67.3 | 17.5 | 8.5 | 3.7 | 3.0 | 0 | | 0.83 |
| 3 | 66.7 | 16.3 | 10.3 | 3.7 | 3.0 | 0 | | 0.83 |
| 4 | 66.1 | 15.2 | 12.1 | 3.7 | 2.9 | 0 | | 0.83 |
| 5 | 68.0 | 17.6 | 8.5 | 2.8 | 3.0 | 0 | NiO:0.1 | 0.83 |
| 6 | 67.8 | 17.0 | 8.5 | 3.6 | 3.0 | 0 | $RuO_2$:0.1 | 0.83 |
| 7 | 67.4 | 17.4 | 8.5 | 3.7 | 0 | 3.0 | | 0.81 |

The glass thus obtained was melted again, and the melt was molded to prepare a column-shaped product of 2 mmϕ × 25 mm in the same manner as in an ordinary method for casting a dental metal. The molded product was then subjected to heat treatment at 700° C. for 16 hours in a mold to crystallize. 5 pieces of the glass-ceramics thus obtained were measured in respect of a bending strength. These glass-ceramics were dipped in an ion exchanged water at 80° C. for 72 hours to measure their weight reduction. The measurement results were shown in Table 2, together with their external appearances.

TABLE 2

| Examples | Bending strength (kg/cm$^2$) | Weight reduction (%) | External Appearance |
|---|---|---|---|
| 1 | 1600 | 0.01 | White translucent |
| 2 | 1700 | 0.00 | White translucent |
| 3 | 1700 | 0.01 | White translucent |
| 4 | 1650 | 0.02 | White translucent |
| 5 | 1800 | 0.01 | Light yellow translucent |
| 6 | 1750 | 0.02 | Light orange translucent |
| 7 | 1700 | 0.01 | White translucent |

EXAMPLES 8 TO 11

Orthophosphoric acid, calcium carbonate, calcium fluoride, strontium carbonate, aluminum oxide, cerium oxide, nickel oxide and ruthenium oxide were mixed in an amount of 400 g in total at such mixing ratios as to provide the composition shown in Table 3, and the resultant mixture was fully mixed (in Table 1, orthophosphoric acid, calcium carbonate and strontium carbonate were expressed in terms of oxides). The mixture thus prepared was calcined at 400° C. for 5 hours, and was then melted in a platinum crucible at 1,300° C. for 1 hour. Thereafter, the fused melt was cast on a stainless steel plate to obtain a glass.

TABLE 3

| Examples | Composition (% by weight) | | | | | | |
|---|---|---|---|---|---|---|---|
| | $P_2O_5$ | CaO | $CaF_2$ | SrO | $Al_2O_3$ | $Ce_2O_3$ | Others |
| 8 | 66.6 | 15.7 | 0.7 | 10.3 | 3.7 | 3.0 | 0 |
| 9 | 66.3 | 14.7 | 2.1 | 10.2 | 3.7 | 3.0 | 0 |
| 10 | 65.8 | 13.6 | 2.1 | 12.0 | 3.5 | 2.9 | NiO 0.1 |
| 11 | 65.5 | 12.5 | 3.5 | 12.0 | 3.5 | 2.9 | $RuO_2$ 0.1 |

The glass thus obtained was melted again, and was molded to obtain a column-shaped product of 2 mmϕ × 25 mm in the same manner as in an ordinary method for casting a dental metal. Thereafter, the column-shaped product was crystallized in a mold by heat treatment at 700° C. for 16 hours.

The glass-ceramic thus obtained was measured in respect of fluorine content by chemical method. The mechanical strength of the glass-ceramic was measured by three-point bending test, thus determining an average value from 5 pieces of column-shaped test samples. A water-resistance was evaluated by measuring weight reduction after dipping the glass-ceramics in water at 80° C. for 72 hours.

In the same manner as above, a disk-like glass-ceramic having a diameter of 16 mm and a thickness of 2 mm was prepared. A fracture toughness was evaluated by polishing the surface of the disk-like glass-ceramic thus prepared, pushing a Vickers indenter on the polished surface under a load of 1 kg for 15 seconds and measuring the length of cracks produced (microindentation method). These results are shown in Table 4, together with external appearances of the glass-ceramics.

TABLE 4

| Examples | F content (% by weight) | Fracture toughness (MNm$^{-3/2}$) | Bending strength (kg/cm$^2$) | Weight reduction (%) | External Appearance |
|---|---|---|---|---|---|
| 8 | 0.3 | 2.8 | 1600 | 0.00 | White translucent |
| 9 | 0.8 | 3.2 | 1700 | 0.00 | White translucent |
| 10 | 0.8 | 3.0 | 1700 | 0.01 | Yellow translucent |
| 11 | 1.3 | 3.2 | 1600 | 0.00 | Orange translucent |

EXAMPLE 12

The starting materials were weighed to mix in an amount of 50 g in total in such a manner as to provide a composition comprising 13 mol % of strontium oxide in terms of SrO, 37 mol % of calcium oxide in terms of CaO and 50 mol % of phosphorus oxide in terms of $P_2O_5$, and the resultant mixture was fully mixed. The mixture thus prepared was melted in a platinum crucible, and the melt was cast on a stainless steel plate to obtain a glass. The glass thus obtained was crystallized by heat treatment at 700° C. for 16 hours to obtain a strontium-containing calcium phosphate crystal. According to X-ray diffraction, the crystal thus obtained was proved to be a calcium β-metaphosphate crystal solid-solubilized with strontium at the position of calcium atom.

This crystal was pulverized into powder having an average particle diameter of 5 μm, and 18 g of the crystal powder thus obtained was mixed with 50 g of a phosphate type invenstment material ("Univest Nonprecious" powder, manufactured by Shofu Inc.). The resultant mixture was kneaded with 17 cc of an ion exchanged water. The kneaded material was cast and cured in a cast ring for dental material having a disk plate-like wax pattern of a diameter of 16 mm and a thickness of 2 mm in the central part. Thereafter, the cast material was heated at 800° C. for 2 hours, and the wax was burnt off to obtain a mold. The mold thus obtained was maintained at 650° C., and a glass composition melted at 1,100° C., which comprises 67% by weight of $P_2O_5$, 16% by weight of CaO, 10% by weight of SrO, 4% by weight of $Al_2O_3$ and 3% by weight of $Ce_2O_3$, was cast by centrifugal cast method. The cast material was then crystallized by maintaining at 700° C. for 16 hours together with the mold.

After the crystallization, the glass-ceramic thus obtained was cooled to room temperature, and was taken out form the mold. The glass-ceramic thus obtained was a translucent and uniformly crystallized product. A Vickers indenter was pushed into the surface of the disk plate, and a fracture toughness was measured by microindentation method. The measured value was 2.5 MNm$^{-3/2}$.

EXAMPLE 13

2 g of calcium phosphate crystal powder solid-solubilized with strontium (average particle diameter: 5 μm) prepared in the same manner as in Example 12 and 5 g of boron nitride powder were mixed with 10 g of an ethyl silicate type binder (HAS-10, manufactured by Colcoat Co., Ltd.), and the resultant mixture was fully kneaded. The slurry thus prepared was coated around a wax pattern having the same shape as in Example 12 in such manner as to provide a thickness of 200 μm, and was dried. Thereafter, a phosphate type investment material ("Univest Nonprecious" powder, manufactured by Shofu Inc.) was cast and cured in usual manner in a cast ring for dental material having the above prepared wax pattern. The mold thus prepared was heat treated at 800° C. for 30 minutes to burn off the wax, thus producing a mold having a layer of a strontium solid-solubilized calcium phosphate crystal formed in an average thickness of 200 μm from the surface.

In the same manner as in Example 12, a glass was cast in the mold thus prepared, and was crystallized in the mold. The glass-ceramic thus obtained was a transparent and uniformly crystallized product. The glass-ceramic had a fracture toughness value of 3.2 MNm$^{-3/2}$ measured in the same manner as in Example 12.

COMPARATIVE EXAMPLE

The starting materials were weighed in an amount of 50 g in total in such a manner as to provide a composition comprising 50 mol % of calcium oxide in terms of CaO and 50 mol % of phosphorus oxide in terms of $P_2O_5$, and the resultant mixture was fully mixed. The mixture thus prepared was melted in a platinum crucible, and the melt was cast on a stainless steel plate to obtain a glass. The glass thus obtained was crystallized by heat treatment at 700° C. for 16 hours. According to X-ray diffraction, the crystal thus obtained was proved to be a calcium β-metaphosphate crystal.

This crystal was pulverized into powder having an average particle diameter of 5 μm, and 18 g of the powder thus prepared was mixed with 50 g of a phosphate type investment material ("Univest Nonprecious" powder, manufactured by Shofu Inc.). The resultant mixture was kneaded with 17 cc of an ion exchanged water, and the kneaded material was cast and cured in a cast ring having a wax pattern of the same shape as in example 12 in the central part. Casting and crystallization were conducted in the same manner as in Example 12 to produce a glass-ceramic.

According to visual evaluation, the glass-ceramic thus produced was a translucent and uniformly crystallized product. The crystallized glass-ceramic had a fracture toughness of 1.8 MNm$^{-3/2}$ measured in the same manner as in Example 12, which was somewhat poor as compared with Examples 12 and 13.

As mentioned above, the glass-ceramic of the present invention has a high mechanical strength, a high chemical durability and an appropriate translucency. Thus, the glass-ceramic of the present invention is quite suitable for a dental material, particularly for a repairing material for a crown of a tooth.

We claim:

1. A calcium phosphate glass-ceramic which comprises from 64 to 72% by weight of phosphorus oxide in terms of $P_2O_5$, from 13 to 20% by weight of calcium oxide in terms of CaO, from 6 to 13% by weight of strontium oxide in terms of SrO, and from 3 to 15% by weight in total of at least one member selected from the group consisting of aluminum oxide, cerium oxide and lanthanum oxide respectively in terms of $Al_2O_3$, $Ce_2O_3$ and $La_2O_3$, a molar ratio of (CaO+SrO)/$P_2O_5$ being 0.78–0.86.

2. The calcium phosphate glass-ceramic according to claim 1, which further contains at least one member selected from the group consisting of elemental substances or compounds of Ni, Fe, Co, Rh, Ru and Pd in an amount of from 0.001 to 3.0% by weight in terms of a metal element.

3. The calcium phosphate glass-ceramic according to claim 1, which further contains fluorine in an amount of from 0.01 to 5.0% by weight in terms of an F atom.

4. The calcium phosphate glass-ceramic according to claim 1, which further contains at least one element selected from the group consisting of Dy, Pr, Tb and Eu in an amount of from 0.001 to 5.0 mol %.

5. A dental material which comprises the calcium phosphate glass-ceramic as defined in claim 1.

* * * * *